(12) United States Patent
Xiong et al.

(10) Patent No.: US 6,475,394 B2
(45) Date of Patent: Nov. 5, 2002

(54) PSEUDO-FOULING DETECTOR AND USE THEREOF TO CONTROL AN INDUSTRIAL WATER PROCESS

(75) Inventors: Kun Xiong, Naperville, IL (US); Gary L. Horacek, Naperville, IL (US); Robert L. Wetegrove, Winfield, IL (US); Rodney H. Banks, Aurora, IL (US)

(73) Assignee: Ondeo Nalco Company, Naperville, IL (US)

( * ) Notice: Subject to any disclaimer, the term of this patent is extended or adjusted under 35 U.S.C. 154(b) by 14 days.

(21) Appl. No.: 09/737,260

(22) Filed: Dec. 13, 2000

(65) Prior Publication Data

US 2002/0108911 A1 Aug. 15, 2002

(51) Int. Cl.[7] .................................................. C02F 1/00
(52) U.S. Cl. ...................... 210/739; 210/764; 210/85; 210/86; 210/97; 210/143; 210/198.1
(58) Field of Search ................................. 210/739, 764, 210/85, 86, 97, 143, 198.1

(56) References Cited

U.S. PATENT DOCUMENTS

| 4,997,574 | A | * | 3/1991 | Sarunac |
| 5,185,533 | A | | 2/1993 | Banks et al. ................. 250/575 |
| 6,023,070 | A | | 2/2000 | Wetegrove et al. ......... 250/573 |
| 6,161,435 | A | * | 12/2000 | Bond et al. |

OTHER PUBLICATIONS

W. H. Dickinson, Biofouling Assessment Using an On–Line Monitor, TAPPI 99 Proceedings, 1999, 445–457.

* cited by examiner

*Primary Examiner*—Betsey Morrison Hoey
(74) *Attorney, Agent, or Firm*—Margaret M. Brumm; Thomas M. Breininger

(57) ABSTRACT

A system and method are provided which enables the monitoring and if desired controlling of fouling within a fluid system. The present invention includes a pseudo-fouling detector system with a pair of identical sensors, where said sensors measure a variable, such as, temperature or pH, in a fluid, producing an electric output representative of the variable. The variable measurements are used to calculate a fouling index which is further used to develop fouling treatment strategies for controlling the amount of fouling in the fluid system.

19 Claims, 2 Drawing Sheets

PSEUDO-FOULING DETECTOR AND USE THEREOF TO CONTROL AN INDUSTRIAL WATER PROCESS

BACKGROUND OF THE INVENTION

The present invention generally relates to systems and methods for industrial water processes. More specifically, the present invention relates to systems and methods that use a detector to monitor and/or control fouling of a fluid within a fluid-containing system.

It is, of course, generally known to provide a fluid system, such as an industrial water process, in which fluid is transported from one location to another location. One such example is a water cooling tower in which heat exchange tubing is provided for transport of water from a first location to a second location. In such a system, undesirable film or fouling is often created on internal surfaces of the tubing. The film typically consists of microorganisms and/or suspended particulate matter that has settled out of the system. The film typically grows in thickness, thus reducing the efficiency of, for example, heat transfer from a hot interior to a cooler ambient environment.

Of course, many other examples of other systems that implement fluid transfer are known. For example, although the fluid may be water, it could be natural gas in a transmission line.

It is generally known that the fouling can be monitored by employing optical detection devices. An example of a known optical detection device for the monitoring of fouling is taught and described in U.S. Pat. No. 5,185,533 (the "533 Patent") to Banks et. al. In the '533 Patent, a system is provided for determining accumulative film thickness at the inside diameter of a main stream conduit by employing an optical fouling meter ("OFM"). The OFM uses two light paths from a single light source. Both light paths pass through a transparent tube although one of the beams of light passes through a section of the tube which is kept free of deposits by a mechanical wiper. This clean section reading allows the reading from the fouled section of the tubing to be corrected for any effects of color or turbidity in the water.

It is desirable to have alternate systems and methods for monitoring and controlling fouling.

SUMMARY OF THE INVENTION

The first aspect of the claimed invention is a system for monitoring fouling in a fluid, the system comprising:

at least one fluid channel for receiving an amount of fluid; at least two identical sensors that measure a certain variable, each sensor adapted to measure the certain variable in the fluid in said fluid channel and produce an electric signal representative of the certain variable; wherein first sensor is permitted to foul and second sensor is cleaned; and a control device for processing the electric signals to calculate a fouling index.

The second aspect of the instant claimed invention is the system of the first aspect of the claimed invention wherein there are at least two fluid channels, wherein said at least two fluid channels are configured parallel to each other and where the same fluid travels each of said at least two fluid channels where said first sensor is configured in the first fluid channel and where said second sensor is configured in the second fluid channel, wherein said first sensor is permitted to foul and wherein said second sensor has been cleaned prior to measuring said variable.

The third aspect of the instant claimed invention is a system for controlling fouling in a fluid, the system comprising:

at least one fluid channel for receiving an amount of fluid; at least two identical sensors that measure a certain variable, each sensor adapted to measure the certain variable in the fluid in said fluid channel and produce an electric signal representative of the certain variable; wherein first sensor is permitted to foul and second sensor is cleaned; and a control device for processing the electric signals to calculate a fouling index and a device for adding a treatment chemical to the fluid dependent on the calculated fouling index.

The fourth aspect of the instant claimed invention is the system of the third aspect of the instant claimed invention wherein there are at least two fluid channels, wherein said at least two fluid channels are configured parallel to each other and where the same fluid travels each of said at least two fluid channels where said first sensor is configured in the first fluid channel and where said second sensor is configured in the second fluid channel, wherein said first sensor is permitted to foul and wherein said second sensor has been cleaned prior to measuring said variable.

The fifth aspect of the instant claimed invention is a method for determining fouling in a fluid, comprising the steps of:

providing at least one fluid channel;

supplying an amount of fluid to said at least one fluid channel;

providing an identical sensor pair that measures a certain variable; wherein the first sensor of said sensor pair is permitted to foul and the second sensor of each sensor pair is cleaned before it measures said certain variable, using said sensor pair to measure the certain variable in the fluid of at least one fluid channel, with each sensor producing a respective electric signal representative of the certain variable; and calculating a fouling index using the electric signals to determine the amount of fouling.

The sixth aspect of the instant claimed invention is the method of the fifth aspect of the instant claimed invention wherein there is provided at least two fluid channels, wherein said at least two fluid channels are configured parallel to each other and where the same fluid travels each of said at least two fluid channels where said first sensor is configured in the first fluid channel and where said second sensor is configured in the second fluid channel, wherein said first sensor is permitted to foul and wherein said second sensor has been cleaned prior to measuring said variable

DETAILED DESCRIPTION OF THE PRESENTLY PREFERRED EMBODIMENTS

The present invention provides improved systems and methods for monitoring fouling within any suitable fluid system, such as, an industrial water process. The present invention also provides, if necessary or desired, a method for controlling fouling in any suitable fluid system, the same.

More specifically, the present invention provides improved systems and methods for monitoring fouling that may use a number of pseudo-fouling detectors, that measure a certain variable, such as temperature or pH. An electric output or signal is generated that is representative of the variable. The variable measurement is then used to calculate a fouling index indicative of an amount of fouling in the fluid system. The fouling index can be further used to monitor and/or control fouling.

Figure 1:
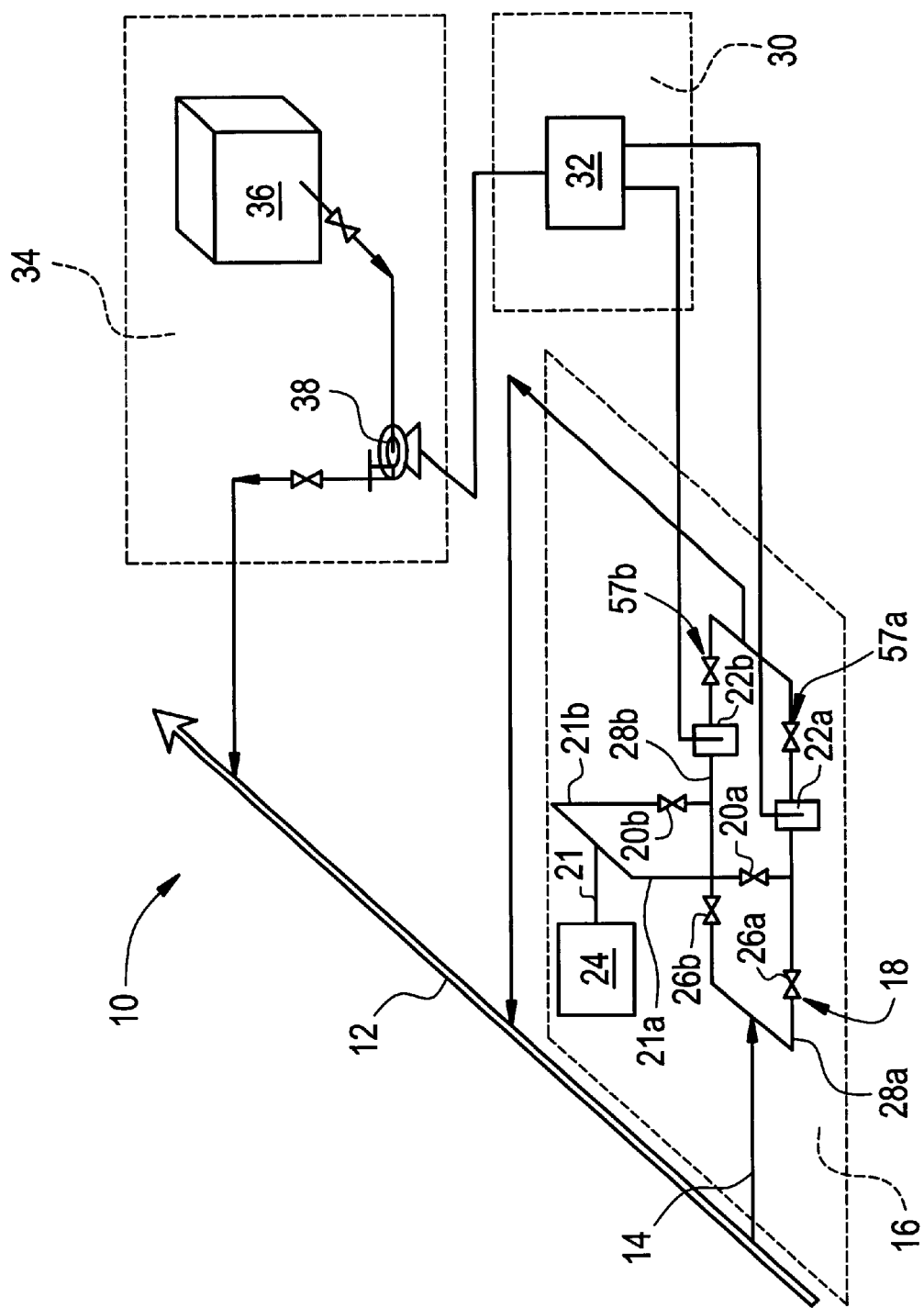
FIG. 1 illustrates a schematic view of a system for monitoring and controlling fluids, as described in the second, fourth and sixth embodiments of the instant claimed invention.

Referring now to FIG. 1, an embodiment of the present invention includes a system for monitoring, and, if desired, controlling, fouling is shown. The system 10 is implemented for monitoring, and, if desired, controlling, fouling that may occur, for example, on walls of a conduit in a fluid-containing system, such as, an industrial water process. To this end, the process water 12 or other like fluids flows in a direction within a conduit (not shown). A sample 14 of the fluid is fed to a pseudo-fouling detector system 16 via a sample conduit.

The pseudo-fouling detector system 16 preferably employs a two-channel detection device 18, e.g., a pseudo-fouling detector device as illustrated in FIG. 1. The device 18 includes first and second flow control valves 26a and 26b in first and second channels 28a and 28b respectively, cleaning system 24, main cleaning system conduit 21, first and second cleaning system flow control valves 20a and 20b in first and second cleaning system conduits 21a and 21b respectively, first sensor 22a and second sensor 22b in first channel 28a and in second channel 28b respectively, and first and second check valves 57a and 57b in first and second channels 28a and 28b respectively.

The pseudo-fouling detector system of the present invention is not limited to the two-channel detector and can include, for example, any suitable number of channels, sensor pairs, cleaning systems, flow control valves, check valves or other like detector components.

First sensor 22a and second sensor 22b are identical and are selected from the group consisting of pH, ion selective electrode, oxidation/reduction potential (hereinafter "ORP"), conductivity, amperometric, chronoamperometric, voltammetric, piezoelectric, fiber optic, spectroscopic, surface plasmon resonance, temperature, oxygen, and capacitance. All of these sensors are known in the art of sensors, and are commercially available from analytical supply companies.

The sample fluid 14 of the process water 12 continuously flows through a first channel 28a and flows through a second or reference 28b channel when fouling data is required. A first sensor 22a and a second sensor 22b are adapted to measure a variable, such as pH, in the fluid supplied by the first channel 28a and the second channel 28b, respectively. First sensor 22a is also referred to as "active" sensor. Second sensor 22b is also referred to as "reference" sensor. In one embodiment, the fluid only flows through the second channel 28b. In this case, the second sensor 22b measures the variable in the sample fluid after second sensor 22b is cleaned with cleaning solution from cleaning system 24. Cleaning system 24 contains a cleaning solution comprising clean water and any necessary chemical cleaning agent required to clean second sensor 22b. Persons of ordinary skill in the art are aware of necessary chemical cleaning agents for each type of sensor. Cleaning system 24 may also be augmented by any necessary mechanical cleaning. Mechanical cleaning systems for sensors are known in the art of sensors.

The configuration shown in FIG. 1 shows that it is possible for cleaning system 24 to clean both first sensor 22a and second sensor 22b. It is possible for cleaning system 24 to clean first sensor 22a by changing the flow of cleaning solution from cleaning system 24 by adjusting valve 20a and valve 20b to permit flow of cleaning solution from cleaning system 24 to first sensor 22a. Being able to clean first sensor 22a is a desirable feature, as eventual fouling of first sensor 22a could render it unable to sense the variable.

In sample channel 28a, check valve 57a prevents water flowing back to sensor 22a. In sample channel 28b, check valve 57b prevents water flowing back to sensor 22b. Once the sample fluid 14 flows through the pseudo-fouling detector system, the sample fluid 14 is then returned to its source, namely, the process water supply 12, or if desired, the sample fluid 14 may be discarded in a manner complying with all environmental laws and regulations.

In the two-channel device 18 as previously described, the present invention includes a pair of calibrated and identical sensors. The first sensor 22a and second 22b sensor measure the variable in the fluid of the first channel 28a and second 28b channel, respectively, and each produce an electric signal or output indicative thereof.

Over time, the first sensor 22a produces a signal that changes with respect to the changing amount of fouling in the process water as well as the changing amount of fouling allowed to build up on first sensor 22a. In contrast, the second or reference sensor 22b provides a signal indicative of a fouling-free measured variable due to the fact that sensor 22b in the second channel is cleaned by cleaning system 24, before it measures the variable. As previously discussed, the second sensor 22b in second channel 28b is either treated or flushed with cleaning solution from cleaning system 24 prior to measuring the variable. Thus, the signal from second sensor 22b remains fouling-free because there is no fouling permitted of second sensor 22b.

As noted above, within the two-channel detection device 18, the first 22a and second 22b sensors must be identical. In addition to requiring identical sensor pairs, the present invention is limited to the type of sensor which either automatically produces an electric output indicative of the measured variable or which can be made to produce an electric output indicative of the measured variable. As mentioned previously, sensors suitable for use in the instant claimed invention are selected from the group consisting of pH, ion selective electrode, oxidation/reduction potential, conductivity, amperometric, chronoamperometric, voltammetric, piezoelectric, fiber optic, spectroscopic, surface plasmon resonance, temperature, oxygen, and capacitance. In the instant claimed invention, these sensors measure the variable that they are designed to measure. For example, the temperature sensor measures the temperature of the fluid and the pH sensor measures the pH of the fluid.

As further shown in FIG. 1, the electric signals from the first 22a and second 22b sensors are transmitted to a control system 30, that includes a control device 32. The control device 32 processes the signals to calculate the fouling index. The calculated fouling index is indicative of the amount of fouling within the process water system. The amount of fouling calculated is based on a fouling index which essentially equals the ratio of the value associated with the electric outputs, generated from each of the first and second sensors. The fouling index is calculated by an onboard computer of the control system and is provided as follows:

$$\text{Fouling Index} = \frac{Output_{sensor2} - Output_{sensor1}}{Output_{sensor2}}$$

Referring to the above Fouling Index equation, sensor 1 and sensor 2 correspond to first sensor 22a and second sensor 22b, respectively. Any suitable arithmetic factor, such as, a multiplying factor, can be included in the fouling index equation for easier use of the calculation, such as, for displaying graphs or analyzing calculation data. For, example, the fouling index can be multiplied by a factor equaling 1000 resulting in a whole number calculation, i.e., 10, rather than a decimal number calculation, i.e., 0.01.

The fouling index is effectively unitless, that is, the fouling index is a ratio of outputs having identical units. For example, if the sensors are temperature sensors measuring a temperature variable (° F.), the units of the fouling index are (° F./° F.).

Once the control system calculates or determines the fouling index, it is compared to a preset control value or preset rate of change that indicates a level which the amount of fouling cannot exceed within the process water supply, i.e., a maximum fouling level or a maximum fouling rate. If the fouling index exceeds this value, or rate, a treatment program or strategy can be developed and applied to treat the process water with an amount of any suitable anti-fouling agent. The optimal treatment program can be determined or based on the fouling index calculations.

In one embodiment, the treatment strategy or program is automatically determined and controlled by the control device 32. As shown in FIG. 1, the control device 32 communicates with a treatment system 34. If the fouling index exceeds the preset control value or preset fouling rate, the control device 32 uses the fouling index to develop the treatment strategy or program. The treatment strategies are derived from any suitable number and variety of treatment models. For example, the process water can be treated with an effective amount of a suitable treatment program, such as any suitable anti-fouling agent or biocidal agent, to prevent fouling within the process stream.

Once developed, the control device 32 communicates with a treatment system 34 to deliver an optimal amount of treatment chemicals 36, to the process water 12 for controlling the amount of fouling in the process water. As shown in FIG. 1, the control device 32 communicates directly with a feeding pump 38 of the treatment system 34. Based on this communication, the feeding pump 38 delivers an amount of treatment chemicals to the process water supply. The feeding pump 38 can deliver the treatment chemicals continuously or intermittently over a predetermined period of time.

It is also possible for control device 32 to communicate with a treatment system 34 where said treatment system 34 provides for treatment chemicals that are added to said process water by other means than feeding pump 38. These types of treatment chemicals are added using mechanisms known to people of ordinary skill in the art of treatment chemicals.

The configuration in FIG. 1 shows first sensor 22a and second sensor 22b in parallel, separate channels 28a and 28b. Those skilled in the art can also recognize that an alternative configuration of sensors is also possible. One such suitable alternative configuration has the first sensor and the second sensor in a single channel, where a cleaning system provides cleaning to the second sensor prior to the second sensor measuring the variable in the sample fluid.

In another embodiment, the treatment strategy or program can be manually developed and applied. In this case, an operator uses the fouling information from the control system, such as, the fouling index calculations, to develop a treatment strategy based on any suitable treatment model. Once the operator develops the strategy, the operator applies this strategy to any suitable treatment system for delivering an optimal amount of treatment chemicals 36 to the process water. For example, the operator can use the feeding pump 38 to deliver an optimal amount of treatment agents. The feeding pump 38 can be semi-automatically controlled by a timing device as set by the operator.

In another embodiment of the present invention, a number of pseudo-fouling detector systems can be used for monitoring and controlling of fouling within a process water supply. The use of multiple pseudo-fouling detector systems enables the monitoring and controlling of fouling within the process water supply at varying locations along the process water supply. The pseudo-fouling detector systems can be operated simultaneously or at staged phases. Each detector system must include a first sensor and a second sensor adapted to measure the variable in a fluid. Each detector system can have one or two channels for the sensors, providing that a cleaning system is provided to clean the second sensor before it measures the variable in the process sample. Although the first and second sensors of each detector system must measure the same variable, each successive pseudo-detector system can include a different sensor pair. For example, the first pseudo-detector system could have two pH meters, the second pseudo-detector system could have two temperature measuring devices and the third pseudo-detector system could have two oxidation-reduction potential sensors.

Figure 2:
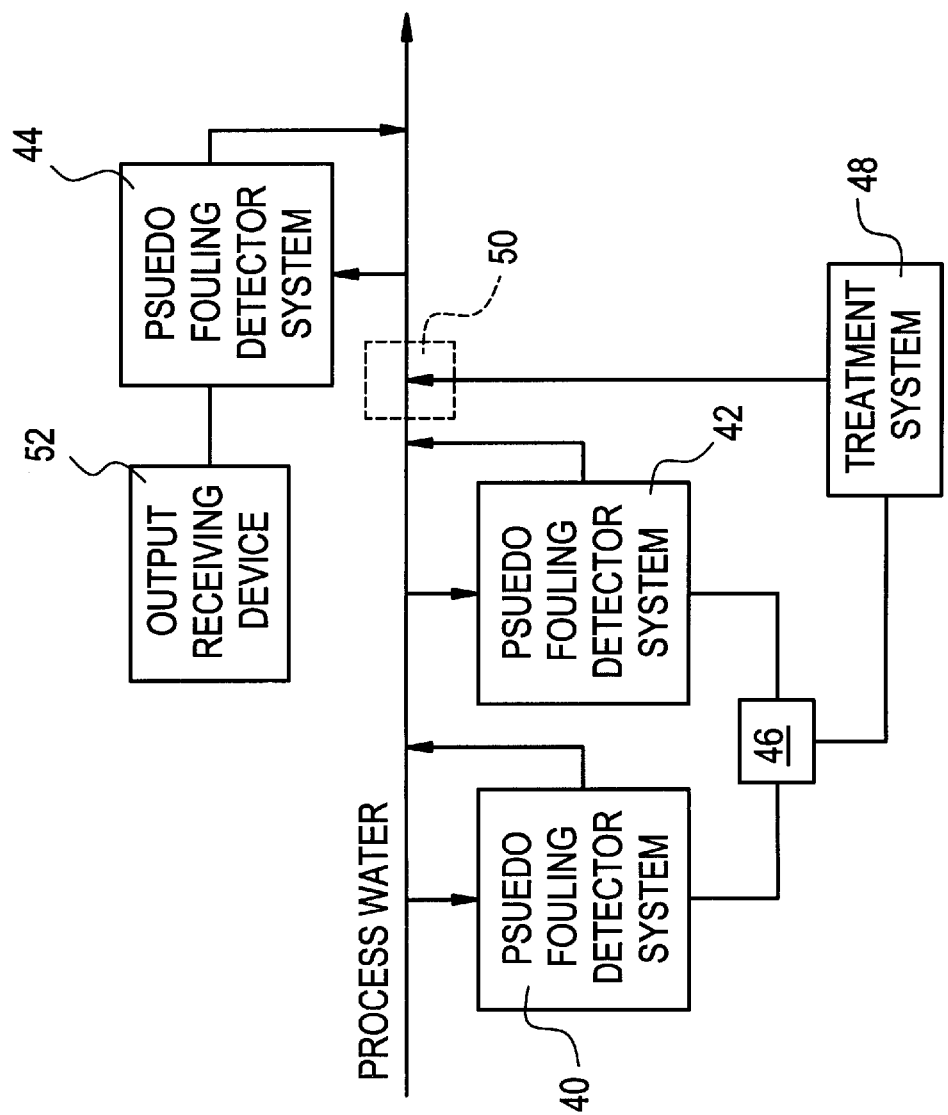
FIG. 2 illustrates a schematic view of an alternate embodiment of a system for monitoring and controlling fluids.

In an embodiment as shown in FIG. 2, the present invention includes a first 40, second 42, and third 44 pseudo-fouling detector system. Each of the pseudo-fouling detector systems includes a first and second sensor as previously discussed. The first and second sensors of each pseudo-fouling detector system are identical and can include any suitable type of sensor that can measure a variable by producing an electric output representative thereof as previously discussed. However, the first and second sensors of the first pseudo-fouling detector system can be different than the first and second sensors of the second and third pseudo-fouling detector system. For example, the sensors of the first, second, and third pseudo-fouling detector systems can include pH, ORP, and temperature sensors, respectively.

As further shown in FIG. 2, the first 40 and second 42 pseudo-fouling detector systems output electric signals as measured by the sensors to a single control device 46 for calculating the fouling index. However, the present invention can include separate control devices for each of the pseudo-fouling detector systems which communicate with, for example, a central control device (not shown). The control device 46 communicates with a treatment system 48 for delivering an optimal amount of anti-fouling agent to the process water supply as previously discussed.

The third pseudo-fouling detector 44 is located downstream of the treatment region 50 of the process water supply. Thus, the third pseudo-fouling detector 44 can be used, but is not limited to, monitoring the process water supply after treatment. The post-treatment monitoring can be conducted to determine the effectiveness of the fouling treatment. The third pseudo-fouling detector 44 measures a variable and outputs an electric signal indicative thereof to an output receiving device 52, such as a control device. The variable measurement data can be used, for example, to calculate a fouling index. The fouling index calculations can be communicated to, for example, the control device 46 such that adjustments can be made to the treatment program or strategy.

EXAMPLE 1

Experimental tests were conducted on a fouling monitoring and/or control system as depicted in FIG. 1. The pseudo-fouling detector included a first or active sensor and a second or reference sensor. The first and second sensors were identical pH sensors. The pseudo-fouling detector was used to monitor a water supply over three separate 72 hour periods. The pH measurements of the sensors were used to calculate a fouling index. In the first 72 hour period, no treatment strategy or program was developed and applied based on the fouling index. In the second and third 72 hour periods, two different treatment programs, namely, treatment programs 1 and 2, were developed and applied for treating the process water with an amount of anti-fouling agent based on the fouling index calculations. The Treatment Programs for each Example are as follows:

Table 1

Program 1: Nalco®N-7648 (active: N-alkyl dimethylbenzylammonium chloride, CAS Registry No. 8001-54-5 and dialkyl methylbenzylammonium chloride, CAS Registry No. 73049-75-9), continuous dosing 50 ppm (0–36 hr) and 25 ppm (36–72 hrs).

Program 2: Nalco®N-7649 (active: 2,2-dibromo-3-nitrilopropionamide, CAS Registry No. 10222-01-2), slug dosing 50 ppm for 1 min every 20 min.

Table 2B:

Program 1: Nalco®N-7648, slug dosing 50 ppm (0–36 hr) and 25 ppm (36–72 hrs) for 1 min every 20 min.

Program 2: Nalco®N-7649, slug dosing 50 ppm for 1 min every 20 min.

Table 3B

Program 1: Nalco®VN-7648, slug dosing 50 ppm (0–36 hr) and 25 ppm (36–72 hrs) for 1 min every 20 min.

Program 2: Nalco®N-7649, slug dosing 50 ppm for 1 min every 20 min.

An Optical Fouling Monitor ("OFM") was used to measure an amount of fouling in the process water after treatment or, comparatively, after no treatment to determine the effectiveness of treatment. The OFM is described in the '533 Patent and U.S. Pat. No. 5,264,917 each of which is herein incorporated by reference.

EXAMPLE 2

Further experimental tests were conducted on the fouling control system as depicted in FIG. 1. These tests were conducted in the same manner as the tests of Example 1 except that the sensors of Example 2 included identical ORP sensors.

EXAMPLE 3

Additional experimental tests were conducted on the fouling control system as depicted in FIG. 1. These tests were conducted in the same manner as the tests of Example 1 except that the sensors of Example 3 included identical temperature sensors.

TESTING RESULTS

The test results for Examples 1–3 demonstrate how the fouling control system of the present invention can be effectively used to monitor and control fouling in a fluid system. The test results of Example 1 are provided in tabular format below in Tables 1A and 1B:

TABLE 1A

Use pH sensors for fouling detection (no treatment)

| | pH Detection | | | |
|---|---|---|---|---|
| Time (hr) | First (Active) Sensor (pH) | Second (Reference) Sensor (pH) | Calculated Fouling Index (pH/pH) | OPM Comparative Fouling Index (mV/mV) |
| 0 | 8.07 | 8.17 | 12.2 | 0 |
| 6 | 8.04 | 8.16 | 14.7 | 155 |
| 12 | 7.95 | 8.10 | 18.5 | 192 |
| 18 | 7.81 | 8.06 | 31.0 | 965 |
| 24 | 7.56 | 8.11 | 67.8 | 900 |
| 30 | 7.50 | 8.12 | 76.4 | 927 |
| 36 | 7.25 | 8.09 | 103.8 | 907 |
| 42 | 6.54 | 8.04 | 186.6 | 1006 |
| 48 | 6.75 | 8.10 | 166.7 | 816 |
| 54 | 6.51 | 8.04 | 190.3 | 649 |
| 60 | 6.47 | 8.07 | 198.3 | 914 |
| 66 | 6.50 | 8.06 | 193.5 | 860 |
| 72 | 6.50 | 8.11 | 198.5 | 766 |

TABLE 1B

Use pH sensors for fouling detection and system control with treatment program 1 and program 2

| | pH Detection with treatment program 1 | | | | pH Detection with treatment program 2 | | | |
|---|---|---|---|---|---|---|---|---|
| Time (hr) | First (Active) Sensor (pH) | Second (Reference) Sensor (pH) | Calculated Fouling Index (pH/pH) | OFM Comparative Fouling Index (mV/mV) | First (Active) Sensor (pH) | Second (Reference) Sensor (pH) | Calculated Fouling Index (pH/pH) | OFM Comparative Fouling Index (mV/mV) |
| 0 | 7.85 | 7.95 | 12.6 | 23 | 7.87 | 7.94 | 8.8 | 20 |
| 6 | 7.99 | 8.13 | 17.2 | 39 | 7.80 | 7.98 | 22.6 | 0 |
| 12 | 8.00 | 8.12 | 14.8 | 0 | 7.87 | 8.02 | 18.7 | 0 |
| 18 | 7.99 | 8.11 | 14.8 | 0 | 7.86 | 8.02 | 20.0 | 43 |
| 24 | 7.92 | 8.03 | 13.7 | 3 | 7.88 | 8.00 | 15.0 | 32 |
| 30 | 7.94 | 8.03 | 11.2 | 0 | 7.92 | 8.04 | 14.9 | 35 |
| 36 | 7.94 | 8.00 | 7.5 | 21 | 7.90 | 8.00 | 12.5 | 43 |
| 42 | 7.86 | 7.94 | 10.1 | 11 | 7.78 | 7.89 | 13.9 | 17 |
| 48 | 7.89 | 8.00 | 13.8 | 0 | 7.83 | 7.91 | 10.1 | 13 |
| 54 | 7.99 | 8.05 | 7.5 | 0 | 7.85 | 7.89 | 5.1 | 24 |
| 60 | 8.04 | 8.11 | 8.6 | 0 | 7.85 | 7.88 | 3.8 | 19 |
| 66 | 8.05 | 8.10 | 6.2 | 0 | 7.80 | 7.81 | 1.3 | 25 |
| 72 | 8.04 | 8.05 | 1.2 | 0 | 7.91 | 7.87 | −5.1 | 24 |

As indicated in Table 1A and 1B, the active sensor produced an electric output as measured in pH level. The pH level varied over time due to the varying amount of fouling in the process water. Therefore, the active pH sensor was responsive to changes in the amount of fouling over time as predicted.

The reference pH sensor, which was cleaned, also produced an electric output based on a measured pH level of the process water.

Based on the active and reference pH sensor measurements, the fouling index was calculated according to the fouling index formula as previously discussed. When there is no fouling, both pH sensors should measure the same pH. When both pH sensors measure the same pH, the calculated fouling index is zero. After fouling begins, the pH sensors will measure different pH, then the calculated fouling index is different than zero.

These calculations were used to develop the different fouling treatment programs, namely, treatment program 1 and treatment program 2. As indicated in Table 1B, treatment program 1 and 2 were effectively applied to control the amount of fouling in the water supply. By comparing the system fouling index results of Tables 1A and 1B, the amount of fouling in the process water after treatment in both treatment program 1 and 2 (as measured by OFM) was markedly lower than the amount of fouling after no treatment (as measured by OFM). Accordingly, the fouling index calculation was effectively used to control fouling as predicted.

The test results of Example 2 are provided in tabular format below in Tables 2A and 2B:

TABLE 2A

Use ORP sensors for fouling detection (no treatment)

| Time (hr) | First (Active) Sensor (mV) | Second (Reference) Sensor (mV) | Calculated Fouling Index (mV/mV) | OFM Comparative Fouling Index (mV/mV) |
|---|---|---|---|---|
| 0 | 223.5 | 212.6 | −51.1 | 0 |
| 6 | 182.6 | 259.5 | 296.2 | 6 |
| 12 | 119.6 | 276.2 | 567.1 | 17 |
| 18 | 41.4 | 259.1 | 840.1 | 800 |
| 24 | −91.8 | 293.1 | 1313.2 | 547 |
| 30 | −200.0* | 247.8 | 1807.0 | 947 |
| 36 | −200.0* | 239.9 | 1833.7 | 816 |
| 42 | −200.0* | 296.4 | 1674.8 | 866 |
| 48 | −200.0* | 270.4 | 1739.7 | 768 |
| 54 | −200.0* | 212.6 | 1941.0 | 862 |
| 60 | −200.0* | 194.4 | 2029.0 | 822 |
| 66 | −200.0* | 205.0 | 1975.6 | 780 |
| 72 | −200.0* | 176.8 | 2131.5 | 650 |

*off-scale, lowest value on the ORP

TABLE 2B

Use ORP sensors for fouling detection and system control with treatment program 1 and program 2

| | ORP Detection with treatment program 1 | | | | ORP Detection with treatment program 2 | | | |
|---|---|---|---|---|---|---|---|---|
| Time (hr) | First (Active) Sensor (mV) | Second (Reference) Sensor (mV) | Calculated Fouling Index (mV/mV) | OFM Comparative Fouling Index (mV/mV) | First (Active) Sensor (mV) | Second (Reference) Sensor (mV) | Calculated Fouling Index (mV/mV) | OFM Comparative Fouling Index (mV/mV) |
| 0 | 121.97 | 156.49 | 220.6 | 8 | 186.1 | 176.5 | −54.1 | 0 |
| 6 | 108.21 | 125.91 | 140.6 | 0 | 307.1 | 318.2 | 35.6 | 172 |
| 12 | 97.07 | 116.23 | 164.8 | 0 | 183.7 | 292.1 | 371.0 | 112 |
| 18 | 96.76 | 104.54 | 74.4 | 0 | 176.8 | 283.2 | 375.8 | 125 |
| 24 | 79.67 | 89.8 | 112.8 | 0 | 176.1 | 263.3 | 331.1 | 122 |
| 30 | 74.03 | 75.58 | 20.5 | 0 | 177.2 | 240.0 | 261.7 | 85 |
| 36 | 66.15 | 87.76 | 246.2 | 0 | 193.8 | 279.4 | 306.3 | 3 |
| 42 | 103.99 | 122.73 | 152.7 | 0 | 174.4 | 265.0 | 341.8 | 78 |
| 48 | 73.29 | 150.9 | 514.3 | 197 | 206.6 | 276.3 | 252.4 | 225 |
| 54 | −198.84 | 231.13 | 1860.3 | 693 | 177.9 | 243.8 | 270.3 | 171 |
| 60 | −200.00 | 200.65 | 1996.8 | 626 | 182.3 | 246.9 | 261.7 | 233 |
| 66 | −20.34 | 207.39 | 1098.1 | 518 | 194.2 | 294.0 | 339.5 | 267 |
| 72 | −189.97 | 198.79 | 1955.6 | 833 | 162.7 | 232.5 | 300.0 | 75 |

As indicated in Tables 2A and 2B, the active ORP sensor produced an electric output as measured in milivolts ("mV"). The mV level varied over time due to the varying amount of fouling in the process water. Therefore, the active ORP sensor was responsive to changes in the amount of fouling over time as predicted.

The reference ORP sensor also produced an electric output as measured in mV for the process water.

Based on the active and reference ORP sensor measurements, the fouling index was calculated according to the fouling index formula as previously discussed. These calculations were used to develop and apply the different fouling treatment programs, namely, treatment program 1 and treatment program 2. By comparing the system fouling index results of Tables 2A and 2B, the amount of fouling in the process water after treatment based on both treatment program 1 and 2 (as measured by OFM) was, in general, markedly lower than the amount of fouling after no treatment (as measured by OFM). Accordingly, the fouling index calculation was effectively used to control fouling.

The test results of Example 3 are provided in tabular format below in Tables 3A and 3B:

TABLE 3A

Use temperature sensors for fouling detection (no treatment)

| | Temperature Detection | | | OFM |
|---|---|---|---|---|
| Time (hr) | First (Active) Sensor (° F.) | Second (Reference) Sensor (° F.) | Calculated Fouling (° F./° F.) | Comparative System Fouling Index (mV/mV) |
| 0 | 118.5 | 123.0 | 37.1 | 18 |
| 6 | 120.3 | 124.3 | 32.0 | 16 |
| 12 | 119.8 | 123.8 | 32.1 | 601 |
| 18 | 117.5 | 122.5 | 40.8 | 614 |
| 24 | 116.3 | 122.9 | 54.2 | 683 |
| 30 | 115.2 | 123.5 | 66.8 | 971 |
| 36 | 114.1 | 123.6 | 76.5 | 1026 |
| 42 | 111.6 | 122.6 | 89.2 | 1083 |
| 48 | 112.8 | 122.9 | 81.9 | 1085 |
| 54 | 114.2 | 124.2 | 80.7 | 1014 |
| 60 | 113.1 | 123.7 | 85.7 | 1062 |
| 66 | 109.9 | 122.9 | 105.7 | 1017 |
| 72 | 109.0 | 122.0 | 106.5 | 799 |

TABLE 3B

Use temperature sensors for fouling detection and system control with treatment program 1 & program 2

| | Temperature Detection with treatment program 1 | | | | Temperature Detection with treatment program 2 | | | |
|---|---|---|---|---|---|---|---|---|
| Time (hr) | First (Active) Sensor (° F.) | Second (Reference) Sensor (° F.) | Calculated Fouling Index (° F./° F.) | OFM Comparative Fouling Index (mV/mV) | First (Active) Sensor (° F.) | Second (Reference) Sensor (° F.) | Calculated Fouling Index (° F./° F.) | OFM Comparative Fouling Index (mV/mV) |
| 0 | 118.2 | 123.0 | 39.5 | 8 | 120.7 | 125.2 | 35.9 | 0 |
| 6 | 120.5 | 124.3 | 31.0 | 0 | 122.8 | 126.9 | 32.1 | 172 |
| 12 | 119.1 | 123.8 | 38.4 | 0 | 122.3 | 126.3 | 32.1 | 112 |
| 18 | 117.4 | 122.5 | 41.9 | 0 | 121.4 | 125.7 | 34.3 | 125 |
| 24 | 117.6 | 122.9 | 43.1 | 0 | 121.5 | 125.7 | 33.6 | 122 |
| 30 | 118.1 | 123.5 | 43.8 | 0 | 123.2 | 126.8 | 27.9 | 85 |
| 36 | 118.0 | 123.6 | 45.1 | 0 | 122.5 | 126.5 | 31.4 | 3 |
| 42 | 115.6 | 122.6 | 56.8 | 0 | 120.8 | 125.3 | 36.5 | 78 |
| 48 | 116.4 | 122.9 | 52.7 | 197 | 122.3 | 126.9 | 36.0 | 225 |
| 54 | 117.8 | 124.2 | 51.6 | 693 | 124.1 | 127.4 | 26.3 | 171 |
| 60 | 116.8 | 123.7 | 55.6 | 626 | 122.2 | 126.6 | 34.5 | 233 |
| 66 | 114.8 | 122.9 | 65.9 | 518 | 119.5 | 124.4 | 39.6 | 267 |
| 72 | 115.2 | 122.0 | 55.9 | 833 | 121.7 | 125.9 | 33.2 | 75 |

As indicated in Tables 3A and 3B, the active sensor produced an electric output as measured in a temperature scale of degrees Fahrenheit ("lF") based on the amount of fouling in the process water. The temperature as measured by the active sensor varied over time due to the varying amount of fouling in the process water. Therefore, the active sensor was responsive to changes in the amount of fouling over time as predicted.

The reference sensor also produced an electric output as measured in a temperature scale of degrees Fahrenheit based on the temperature of the process water.

Based on the active and reference sensor measurements, the fouling index was calculated according to the fouling index formula as previously discussed. These calculations were used to develop and apply the different fouling treatment programs, namely, treatment program 1 and treatment program 2. By comparing the system fouling index results of Tables 3A and 3B, the amount of fouling in the process water after treatment based on both treatment program 1 and 2 (as measured by OFM) was, in general, markedly lower than the amount of fouling after no treatment (as measured by OFM). Accordingly, the fouling index calculation was effectively used to control fouling.

As a result of the systems and methods of the present invention, a low cost, highly reliable system for monitoring fouling and effecting feeding of anti-fouling and biocidal treatment is provided.

It should be understood that various changes and modifications to the presently preferred embodiments described therein will be apparent to those skilled in the art. Such changes and modifications can be made without departing from the sphere and scope of the present invention and without diminishing its intended advantages. It is therefore intended that all such changes and modifications be covered by the intended claims.

What is claimed is:

1. A system for monitoring fouling of surfaces in contact with a fluid, the system comprising:
at least one fluid channel for receiving an amount of fluid;
at least two identical sensors that measure a certain variable, each sensor adapted to measure the certain variable in the fluid in said fluid channel and produce an electric signal representative of the certain variable; wherein the surface of the first sensor, that is in contact with the fluid, is permitted to foul and the surface of second sensor, that is in contact with the fluid, is cleaned; and a control device for processing the electric signals to calculate a fouling index.

2. The system of claim 1 further comprising a treatment system for treating the fluid to reduce the fouling on the surfaces in contact with said fluid, wherein said treatment system is operated based upon a calculated fouling index.

3. The system of claim 1 wherein there are at least two fluid channels, wherein said at least two fluid channels are configured parallel to each other and where the same fluid travels each of said at least two fluid channels, wherein said first sensor is configured in the first fluid channel, and wherein said second sensor is configured in the second fluid channel, wherein the surface of said first sensor that is in contact with the fluid is permitted to foul and wherein the surface of second sensor that is in contact with the fluid has been cleaned prior to measuring said variable.

4. The system of claim 3 wherein the sensors are selected from the group consisting of pH, ion selective electrode, oxidation/reduction potential, conductivity, amperometric, chronoamperometric, voltammetric, piezoelectric, fiber optic, spectroscopic, surface plasmon resonance, temperature, oxygen and capacitance.

5. The system of claim 1 wherein the sensors are selected from the group consisting of pH, ion selective electrode, oxidation/reduction potential, conductivity, amperometric, chronoamperometric, voltammetric, piezoelectric, fiber optic, spectroscopic, surface plasmon resonance, temperature, oxygen and capacitance.

6. The system of claim 1 wherein the fouling index is calculated by the formula:

$$fouling\ index = \frac{Output_{sensor2} - Output_{sensor1}}{Output_{sensor2}},$$

where Output sensor is the processed electric signal of the first sensor and $Output_{sensor\ 2}$ is the processed electric signal of the second sensor.

7. The system of claim 6 further comprising a treatment system for treating the fluid to reduce the fouling on the surfaces in contact with said fluid; where the treatment system is activated if the calculated fouling index is greater than a preset control value or the rate of change of the calculated fouling index is greater than a preset control rate of change.

8. A system for controlling fouling of surfaces in contact with a fluid, the system comprising:
a) at least one fluid channel for receiving an amount of fluid;
b) at least two identical sensors that measure a certain variable, each sensor adapted to measure the certain variable in the fluid in said fluid channel and produce an electric signal representative of the certain variable; wherein the surface of said first sensor that is in contact with the fluid is permitted to foul and the surface of said second sensor that is in contact with the fluid is cleaned;
c) a control device for processing the electric signals to calculate a fouling index; and,
d) a device for adding a treatment chemical to the fluid, wherein the amount of treatment chemical added is dependent on the calculated fouling index.

9. The system of claim 8 wherein the first sensor and second sensor are selected from the group consisting of pH, ion selective electrode, oxidation/reduction potential, conductivity, amperometric, chronoamperometric, voltammetric, piezoelectric, fiber optic, spectroscopic, surface plasmon resonance, temperature, oxygen and capacitance.

10. The system of claim 8 further comprising providing at least two fluid channels, wherein said at least two fluid channels are configured parallel to each other and where the same fluid travels each of said at least two fluid channels, wherein said first sensor is configured in the first fluid channel, and wherein said second sensor is configured in the second fluid channel, wherein the surface of said first sensor that is in contact with the fluid is permitted to foul and wherein the surface of said second sensor that is in contact with the fluid has been cleaned prior to measuring said variable.

11. The system of claim 8 wherein the fouling index is calculated based on the formula:

$$fouling\ index = \frac{Output_{sensor2} - Output_{sensor1}}{Output_{sensor2}},$$

where $Output_{sensor\ 1}$ is the processed electric signal of the first sensor and $Output_{sensor\ 2}$ is the processed electric signal of the second sensor.

12. The system of claim 8 wherein said control device automatically adds a treatment chemical to the fluid to reduce the fouling of surfaces in contact with the fluid, wherein said treatment chemical is added if the calculated fouling index exceeds a certain preset value or the rate of change of the calculated fouling index exceeds a certain preset rate of change.

13. A method for determining fouling of surfaces in contact with a fluid comprising the steps of:
  a) providing at least one fluid channel;
  b) supplying an amount of fluid to said at least one fluid channel;
  c) providing an identical sensor pair that measures a certain variable, wherein the surface of the first sensor that is in contact with the fluid is permitted to foul, and the surface of the second sensor that is in contact with the fluid is cleaned before said second sensor measures a certain variable;
  d) using each sensor to measure the certain variable in the fluid and produce a electric signal representative of the certain variable; and
  e) calculating a fouling index using the electric signals to determine the amount of fouling.

14. The method of claim 13 further comprising the step of
  f) treating the fluid to reduce the fouling of the surface in contact with the fluid, wherein the amount of treatment chemical added is dependent upon the calculated fouling index.

15. The method of claim 13 wherein the measuring step includes measuring the variable by employing the sensor pair selected from the group consisting of pH, ion selective electrode, oxidation/reduction potential, conductivity, amperometric chronoamperometric, voltammetric, piezoelectric, fiber optic, spectroscopic, surface plasmon resonance, temperature, oxygen and capacitance.

16. The method of claim 13 further comprising treating the fluid to reduce the fouling of the surface in contact with the fluid, wherein treatment chemical is added if the calculated fouling index is greater than a preset control value or the rate of change of the calculated fouling index is greater than a preset control rate of change.

17. The method of claim 13 wherein the treating step further includes manually treating the fluid to reduce the fouling of the surface in contact with the fluid.

18. The method of claim 13 wherein the calculating step includes the fouling index having the formula:

$$fouling\ index = \frac{Output_{sensor2} - Output_{sensor1}}{Output_{sensor2}},$$

where $Output_{sensor\ 1}$ is the processed electric signal of the first sensor and $Output_{sensor\ 2}$ is the processed electric signal of the second sensor.

19. A method for determining fouling of surfaces in contact with a fluid comprising the steps of:
  a) providing at least two fluid channels, wherein said at least two fluid channels are configured parallel to each other and where the same fluid travels each of said at least two fluid channels;
  b) supplying an amount of said fluid to said at least two fluid channels;
  c) providing an identical sensor pair that measures a certain variable, wherein the surface of the first sensor, that is in contact with the fluid, is permitted to foul, and the surface of the second sensor, that is in contact with the fluid, is cleaned before said second sensor measures a certain variable, wherein said first sensor is configured in the first fluid channel, and wherein said second sensor is configured in the second fluid channel;
  d) using each sensor to measure the certain variable in the fluid and produce a electric signal representative of the certain variable; and
  e) calculating a fouling index using the electric signals to determine the amount of fouling.

* * * * *